United States Patent [19]

Steppuhn et al.

[11] Patent Number: 5,385,903
[45] Date of Patent: Jan. 31, 1995

[54] PHARMACEUTICAL AGENT FOR TREATMENT OF WITHDRAWAL SYMPTOMS

[75] Inventors: Karin G. Steppuhn; Karin Bressler; Martin Gieseler; David N. Stephens; Lechoslaw Turski, all of Berlin, Germany

[73] Assignee: Schering Aktiengesellschaft, Berlin and Bergkamen, Germany

[21] Appl. No.: 910,873

[22] Filed: Jul. 9, 1992

[30] Foreign Application Priority Data

Jul. 9, 1991 [DE] Germany .............................. 4123106

[51] Int. Cl.⁶ ................. A61K 31/495; A61K 31/675; A61K 31/66
[52] U.S. Cl. ..................... 514/249; 514/85; 514/120; 514/812
[58] Field of Search ................. 514/249, 120, 85, 812, 514/249

[56] References Cited

U.S. PATENT DOCUMENTS 4,975,430 12/1990 Jahr et al. ............................ 514/255
5,095,009 3/1992 Whitten et al. ........................ 514/85

OTHER PUBLICATIONS

McCaslin et al., CA107(11):89773c (Chem. Abstracts) 1987.
Jpn. J. Pharmacol., vol. 55, Suppl. 1 (1991) p. 298P.
Brain Research, 552, (1991) pp. 295-300.
Akaoka, H. et al., J. of Neruorscience, Dec. 1991, vol. 11, No. 12, pp. 3830-3839.
Postgraduate Med. Journal (1988), vol. 64, (Suppl 2), pp. 40–44.

Primary Examiner—Marianne M. Cintins
Assistant Examiner—William R. A. Jarvis
Attorney, Agent, or Firm—Millen, White, Zelano, & Branigan

[57] ABSTRACT

The use of the non-NMDA receptor antagonists quisqualate or kainate antagonists or their physiologically compatible salts for treatment of withdrawal symptoms after drug abuse as well as the combination of the new pharmaceutical agents with NMDA antagonists are described.

11 Claims, 3 Drawing Sheets

PHARMACEUTICAL AGENT FOR TREATMENT OF WITHDRAWAL SYMPTOMS

BACKGROUND OF THE INVENTION

The invention relates to the use of non-NMDA antagonists or their physiological salts for the production of pharmaceutical agents for treatment of withdrawal symptoms after drug abuse as well as the combination of the pharmaceutical agents with NMDA antagonists.

Both in clinical studies and in practice, frequently long-term treatments with benzodiazepine-receptor-binding pharmaceutical agents, such as, e.g., diazepam (valium), are performed in spasmodic conditions and sleep disturbances or for sedation and reducing anxiety. The greatest problem for the patients are the withdrawal symptoms occurring after discontinuing these substances. Symptoms include muscular stiffness, tremor, seizures and anxiety conditions. These withdrawal symptoms also occur after intake of drugs or substances with abuse potential, especially after discontinuing the treatment with pharmaceutical agents which cause an addiction, such as, for example, benzodiazepines, opiates, hallucinogens, barbiturates, after use of other narcotics such as cocaine or heroin, or after the use of alcohol. As substances which can cause a physical and psychological dependence, the following can be mentioned as examples:

1. Opiates such as morphine and its derivatives, as well as substances with a morphine effect such as methadone, pethidine and meperidine as well as codeine and heroin;
2. Hallucinogens such as fentanyl, α-methylfentanyl, 3-methylfentanyl, etryptamine, dimethyltryptamine and amphetamines, for example, amphetamine, methamphetamine, phenmetrazine, methylphenidate and dexamphetamine;
3. Compounds with sedative effects, such as benzodiazepines, for example, diazepam and chlordiazepoxide, meprobamate and barbiturates, for example, hexobarbital, phenobarbital and heptabarbital;
4. Alcohols such as ethanol, and
5. Alkaloids, such as cocaine.

The role of excitatory amino acids in the central nervous system has gained increasing interest in recent years. Glutamate thus was identified as a neurotransmitter and three other receptor subtypes for excitatory amino acids were found and characterized, which were named after the specifically effective glutamate-analogous amino acids N-methyl-D-aspartate (NMDA), kainate and quisqualate receptors.

The benzodiazepines are psychopharmaceutical agents for which it is best known that the long-term treatment, as has been proved, to lead to tolerance and dependence. A sudden interruption in the intake can result in undesirable withdrawal symptoms such as seizures, muscular stiffness and anxiety conditions, whose mechanisms until now have been largely unclarified since sensitive methods for the objective description of the withdrawal symptoms are lacking in animal experiments.

Withdrawal is considered as a time-dependent but homogeneous clinical and pathophysiological process whose symptoms are attributable to the presence of a gamma-aminobutyrate-BDZ/Cl of an ionophoric receptor-effector complex.

SUMMARY OF THE INVENTION

It has surprisingly been found that excitatory amino acids are involved in the development of the dependence and that the blocking of the quisqualate or kainate receptor in the withdrawal prevents or reduces the symptoms of the withdrawal.

An object of the invention is the use of non-NMDA antagonists, i.e., kainate or quisqualate receptor antagonists or their physiologically compatible salts for the production of pharmaceutical agents for the treatment of withdrawal symptoms after discontinuing the treatment with sedative substances, opiates, hallucinogens or other narcotics such as cocaine or heroin or after the intake of alcohol.

A further object of the invention is further the use of non-NMDA antagonists or their salts for the production of pharmaceutical agents for suppression of dependence on drugs or on pharmaceutical agents or substances with abuse potential.

The methods for detecting withdrawal symptoms are based on the conduction of electrical potentials of the brain (EEG), the electromyographic conduction of muscular activity (EMG) and the exploratory activity during the withdrawal in mice as is shown by the example of the withdrawal symptoms after benzodiazepine withdrawal.

Seizures, muscular spasms and anxiety conditions are among the most known withdrawal symptoms, which occur after discontinuation of a long-term treatment with BDZ in humans. To examine the withdrawal symptoms and signs after long-term administration of benzodiazepine, male NMRI mice weighing 20–24 g were made tolerant under daily controlled conditions (0600–1800 hours of bright/dark rhythm, 45–55% atmospheric humidity and free access to water and food) for 12 days with 15 mg/kg of diazepam in sesame oil by subcutaneous injection. The control animals were treated under the same conditions for 12 days with the vehicle s.c. The twelve-day treatment with 15 mg/kg of diazepam in mice leads to a total tolerance in the sedative, anticonvulsive and anxiolytic property. The recording of the withdrawal symptoms was begun one day after the last subcutaneous injection. This day was called the first withdrawal day. With this day, all animals receive a daily s.c. injection with the vehicle.

The recording of the spontaneously occurring seizures was performed with the help of a video- and computer-controlled EEG recording system. This system makes possible a simultaneous video recording of eight animals simultaneously. For the conduction of the EEG, a deep hippocampal electrode and a superficial cortical electrode each were implanted in the animals. The recordings were made on 21 successive days with short daily thirty-minute breaks (between 0830 and 0900 hours) to tend to the animals.

The study of the muscle tone changing in the withdrawal was derived with the help of the EMG of M. gastrocnemius. For this purpose, the mice were placed in ventilated individual boxes. Their hind legs were stretched through two holes in the bottom of the boxes and attached carefully with adhesive strips.

The study on anxiety conditions was tested with the help of a specially designed locomotion position. For this purpose, the animals were placed in individual boxes, which recorded the movements of the animals by light barriers. The back and forth movement on only one side of the locomotion boxes or the remaining in a corner was used as a measurement for anxiety.

Excitatory amino acids (EAA), especially the L-glutamate receptor subtypes such as N-methyl-D-aspartate (NMDA), alpha-amino-3-hydroxy-5-tert-butyl-4-isoxazolepropionate (ATPA) and kainate (KA), have the ability to induce seizures in intracerebroventricular administration. The seizure threshold of the excitatory amino acids was tested on 21 days in the withdrawal by an intracerebroventricular infusion in freely moving mice. This type of administration was selected since these amino acids only pass the blood-brain barrier with difficulty.

Further, the spinal reflexes were tested on 21 days in diazepam withdrawal, which were derived under a chloralose/urethane anesthesia. The Hoffmann Reflex (H-) is a monosynaptic reflex and dependent on the AMPA receptors, which are named after the specific agonists (RS)-α-amino-3-hydroxy-5-methyl-4-isoxazolepropionate (non-NMDA receptors). In contrast to that, the flexion reflexes are polysynaptic and NMDA conveyed. For the conduction of the H reflex, the N. tibialis was stimulated one to three times with regulated current surges. The electrodes used in this case were superficially attached to the plantar muscle of the foot. The conduction of the flexion reflexes (stimulus threshold and EMG of the nerves) was made by M. tibialis by five electric pulses one to three times in a series. For this purpose, the electrode pair was applied percutaneously in the ipsilateral M. tibialis.

The results of the animal tests are to be interpreted as follows:

The seizure threshold, induced by ATPA and KA in diazepam withdrawal was reduced on the second and third day and from day four until day twenty-one no longer differed from that of the control animals. At the same time on days two and three, the seizure threshold for NMDA remained at the control level. On days four to seven, however, a reduction of the NMDA seizure threshold was observed, which, however, was again normalized on or before day twenty-one (FIG. 1).

The conduction of the Hoffmann Reflex shows an increase of the threshold value during the first three days of the withdrawal. But the maximum flexion reflex was at a later time, between days four and twenty-one.

In the EMG, an increase of the muscle tone was observed starting from the fourth day, which, however, was again reduced to the control level on or before day twenty-one (FIG. 2B).

In the study on anxiety conditions in withdrawal, a changed movement behavior of the animals was shown from day four. They moved preferably into a corner or ran along only one wall of the locomotion boxes, while the control animals used the entire space available to them and ran around all over in the boxes (FIG. 2C).

The electroencephalographic recording of the brain currents of the animals continuing over twenty-one days indicates seizure potentials from day four, which again quiet down only on or before the end of the twenty-first day (FIG. 2A).

This data shows that the withdrawal of diazepam in mice can be shown and quantified with the help of electrophysiological methods. EEG, EMG and the activity measurement represent reliable methods to detect the withdrawal symptoms. The long-term conduction in the EEG shows that in the withdrawal, two important clinically relevant phases can be distinguished. The seizure threshold experiments with selective antagonists and the reflex pharmacology show that the initial phase of the diazepam withdrawal functions by the non-NMDA mechanism. This first phase is very short and asymptomatic but certainly decisively involved in the development of the second symptomatic phase. The first phase is designated as "silent" and the second phase as "active."

From the results, it can be seen that the "silent phase" is imparted by non-NMDA mechanisms and the "active phase" by NMDA mechanisms.

To study the additional role of the excitatory amino acids in the "silent phase" in the withdrawal of substances with a sedative effect, the animals were treated with quisqualate antagonists or NMDA antagonists. In this case, minipumps having an osmotic effect were implanted intraperitoneally in the "silent phase" in the diazepam withdrawal under a light ether anesthesia and the withdrawal symptoms in the EEG, EMG and the locomotion unit were examined from day two to day twenty-one. The pumps were filled in advance with quisqualate antagonists or NMDA antagonists. The pump rate was 10 mg/kg/h over 72 hours.

By the treatment with quisqualate antagonists during the first 3 days of the diazepam withdrawal, the development of seizures and the increase of the muscle tone are prevented and the anxiety of the animals is reduced as is shown by the example of the treatment with NBQX (FIG. 3). In contrast to this, the three-day infusion of NMDA antagonists such as CPP (3-((±12-carboxy-piperazin-4-yl)-propyl-1-phosphonic acid) shows no elimination of the withdrawal symptoms (FIG. 3).

The fact that the first phase is decisive for the clinical results is shown by the use of the quisqualate antagonist NBQX in the "silent phase," which completely prevents the development of the clinical symptoms, and that in contrast to this, the NMDA antagonist CPP has no influence whatsoever on the development of the withdrawal symptoms.

The blocking of the non-NMDA receptor in the first phase of the withdrawal (silent phase) is sufficient to reduce or to prevent the development of the symptomatic phase.

These studies show that the treatment during the first phase of the withdrawal with non-NMDA antagonists determines the subsequent clinical results and prevents the development of withdrawal symptoms.

Quisqualate antagonists with a selective and nonselective effect on AMPA receptors, which are described, for example, in EP-A-374534, EP-A-348872, EP-A-283959, EP-A-377112, EP-A-315959, Danish patent applications Nos. 1622/91, 1623/91, 1624/91 and 0730/91 and German patent application P 41 35 871.6, and noncompetitive quisqualate antagonists, such as, e.g., GYKI 52466 (1-(4-aminophenyl)-4-methyl-7,8-methylene-dioxy-5H-2,3-benzodiazepine): Tofisopam, Ro 15-1788 (ethyl-8-fluoro-5,6-dihydro-5-methyl-6-oxo-4H-imidazo(1,5a)(1,4)benzodiazepine-3-carboxylate and the β-carbolines and quisqualate antagonists with a selective or nonselective effect on metabotropic receptors mentioned in German patent application P 42 12 529.4 such as, e.g., L-2-amino-4-phosphonobutyric acid (AP4) or L-2-amino-3-phosphonopropionic acid (AP3) and kainate antagonists such as γ-glutamylaminomethylsulfonic acid, as well as their physiologically compatible salts, which are derived from alkali or alkaline-earth metals or the usual inorganic and organic acids such as hydrochloric acid, hydrobromic acid, sulfuric acid, phosphoric acid, citric acid, maleic acid or fumaric acid, are suitable according to the invention. Quinoxaline derivatives and their tautomeric forms with a selective and nonselective effect on AMPA receptors are especially suitable.

Preferred embodiments are quinoxalinedione derivatives and their tautomeric forms of formula I

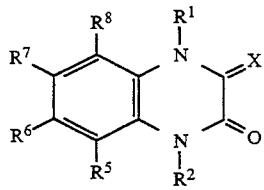

in which $R^1$ and $R^2$ each represent hydrogen or a substituent mentioned in the cited patents and X means oxygen or, together with $R^1$ the grouping =N—NR$^3$—CO— or the grouping =N—N=CR$^3$ and $R^5$, $R^6$, $R^7$ and $R^8$ are the same or different and each mean hydrogen, $NO_2$, $NH_2$, cyano, halogen (fluorine, chlorine, bromine or iodine), $CF_3$, $SO_2NR'R'$, $SO_2R'$ or $OR'$ and R' is hydrogen or $C_{1-4}$ alkyl or $R^5$ and $R^6$ or $R^7$ and $R^8$ respectively together mean a fused benzene or hetaryl ring or —(CH$_2$)$_4$— and $R^3$ is hydrogen, $C_{1-6}$ alkyl or $CF_3$, and the benzene or hetaryl radical can be substituted the same or different one to three times with $NO_2$, $NH_2$, cyano, halogen, $CF_3$, $SO_2NR'R'$ $SO_2R'$ or $OR'$ in which R' has the above-mentioned meaning. Suitable hetaryl rings are pyridine, pyrazole, thiophene, pyrazine, triazole, imidazole, suitable substituents $R^1$ and $R^2$ are $C_{1-12}$ alkyl, $C_{3-8}$ cycloalkyl, $C_{4-8}$ cycloalkylalkyl optionally substituted with hydroxy, $NH_2$, carboxy, carboxylic acid esters, carboxylic acid amides, phosphonic acid, phosphonic acid ester or phosphonic acid amides, $C_{6-10}$ aryl, especially phenyl, optionally substituted with phosphonic acid, phosphonic acid esters or phosphonic acid amides, $C_{7-11}$ aralkyl, especially benzyl, $C_{2-7}$ alkanoyloxy, hydroxy, $C_{1-6}$ alkoxy, $C_{6-10}$ aryloxy, especially benzyloxy, $C_{3-8}$ cycloalkyloxy and $C_{4-8}$ cycloalkylalkyloxy optionally substituted with phosphonic acid, phosphonic acid esters or phosphonic acid amides.

Especially preferred are quinoxaline and benzoquinoxaline derivatives, their tautomeric forms and salts, which optionally are substituted once to twice with $NO_2$, halogen, $C_{1-6}$ alkyl, cyano, $CF_3$, $SO_2NR'R'$, $SO_2R'$ or $OR'$, in which R' is hydrogen or $C_{1-4}$ alkyl and $R^1$ and $R^2$ are the same or different and mean hydrogen or $C_{1-12}$ alkyl optionally substituted with —CO—$R^4$, —POXY, $NR^7R^8$ or phenyl and X means oxygen or $R^1$ and X together mean the groupings =N—NR$^3$—CO— or =N—N=CR$^3$— in which $R^3$ is hydrogen, $C_{1-6}$ alkyl or $CF_3$ and $R^4$, X and Y each mean hydroxy, $C_{1-6}$ alkoxy or $NR^7R^8$ and $R^7$ and $R^8$ are the same or different and are hydrogen, $C_{1-6}$ alkyl or together with the nitrogen atom form a saturated 5- or 6-membered heterocycle, which can contain another O—, N— or S— atom such as piperidine, pyrrolidine, morpholine, thiomorpholine or piperazine.

Quite especially preferred, for example, there can be mentioned 6-nitro-7-sulfamoylbenzo[f]-quinoxaline-2,3-(1H,4H)-dione (NBQX), 6,7-dinitroquinoxaline-2,3-dione (DNQX) and 6-cyano-7-nitroquinoxaline-2,3-dione (CNQX).

In contrast to the quisqualate antagonist NBQX, which completely prevents the development of clinical symptoms in the "silent phase," the NMDA antagonist CPP has no influence whatsoever on the development of the withdrawal symptoms. In the animals with CPP treatment, the withdrawal symptoms and signs were faster and more pronounced than in the comparable control animals. The electrographically recorded seizures lasted longer, were generalized and had a higher frequency. The same was shown in the EMG, in which the muscular activity was greatly increased. The results show that the activation of the non-NMDA receptors before the NMDA receptors is necessary for the triggering of the withdrawal symptoms.

This invention also relates to the use of non-NMDA antagonists in combination with NMDA antagonists for the treatment of withdrawal symptoms and/or suppression of dependence after drug abuse. Preferably a two-phase combination is used, in which non-NMDA antagonists are administered in the first phase and NMDA antagonists in the subsequent phase.

As suitable NMDA antagonists, there can be mentioned as examples:

Competitive antagonists—2-amino-7-phosphonoheptanoic acid (AP 7) and analogs; 3-((±)2-carboxy-piperazin-4-yl)-propyl-1-phosphonic acid (CPP) and analogs; (e)-4-(3-phosphonoprop- 2-enyl)piperazine-2-carboxylic acid (CPP-enes) and analogs;

S-α-amino-5-phosphonomethyl-[1,1'-biphenyl]-3-propanoic acid,

E-2-amino-4-methyl-5-phosphono-3-pentenoic acid,

E-2-amino-4-methyl-5-phosphono-3-pentenoic acid ethyl ester, cis-4-phosphonomethyl-2-piperidinecarboxylic acid, (R)-4-oxo-2-amino-5-phosphono-pentanoic acid, 2-amino-4,5-(1,2-cyclohexyl)-7-phosphonoheptanoic acid, 4-(phosphonomethyl)-DL-phenylglycine, 4-(3-phosphonopropyl)-2-piperidinecarboxylic acid, 2-(2-phosphonoethyl)-DL-phenylalanine, 3-carboxy-5-(phosphonoethyl)-1,2,3,4-tetrahydroisoquinoline, 3-carboxy-5-phosphono-1,2,3,4-tetrahydroisoquinoline, cis-DL-4-[(1(2)H-tetrazol-5-yl)methyl]-2-piperidinecarboxylic acid, cis-4-(3-phosphonoprop-1-enyl)-2-piperidinecarboxylic acid, E-2-amino-4-propyl-5-phosphono-3-pentenoic acid, phosphoric acid-4-(2-carboxy-piperidinyl)ester and 1-[4(4-chloro-α,α-dimethylbenzyl)-2-methoxyphenyl]-1,2,4-triazole-3-carboxylic acid amide, cis-4-phosphonomethyl-2-piperidincarboxylic acid (CGS 19755); DL-(E)-2-amino-4-methyl-5-phosphono-3-pentanoic acid (CGP 40116) enantiomers and analogs;

noncompetitive antagonists (+)10,11-dihydro-5-methyl-5H-dibenzo-[a,d]-cycloheptan-5,10-imine (MK-801) and analogs; memantines and other amantadine analogs; ketamine and analogs; budipine and analogs; ifenprodil and analogs; antagonists of the glycine binding site—kynurenic acid and analogs; 1-hydroxy-3-amino-pyrrolidin-2-one (HA-966) and analogs; polyamines—spermine and spermidine and analogs; inhibitors of the excitatory amino acid synthesis.

Competitive NMDA antagonists can be considered as preferred.

The invention also comprises pharmaceutical agents which contain the above-mentioned compounds in their effective amount, their production as well as the use of compounds for the production of pharmaceutical agents, for treatment and prophylaxis of the above-mentioned withdrawal symptoms and signs as well as for suppression of dependence after intake of substances with abuse potential. The pharmaceutical agents are produced according to processes known in the art, by the active ingredient, with suitable vehicles, auxiliary agents and/or additives, being brought into the form of a pharmaceutical preparation, which is suitable especially for enteral or parenteral administration.

The administration can take place orally or sublingually as a solid in the form of capsules or tablets or as a liquid in the form of solutions, suspensions, elixirs or emulsions or rectally in the form of suppositories or in the form of injection solutions that optionally can also be administered subcutaneously. As auxiliary substances for the desired pharmaceutical agent formulation, the inert organic and inorganic vehicles known to one skilled in the art are suitable, such as, e.g., water, gelatin, gum arabic, lactose, starch, magnesium stearate, talc, vegetable oils, polyalkylene glycols, etc. Further, preservatives, stabilizers, wetting agents, emulsifiers or salts to change the osmotic pressure or buffers optionally can be comprised.

The pharmaceutical preparations can be present in solid form, for example, as tablets, coated tablets, suppositories, capsules or in liquid form, for example, as solutions, suspensions or emulsions, or can be formulated as a depot preparation.

As vehicle systems, interface-near auxiliary agents such as salts of bile acids or animal or vegetable phospholipids, but also mixtures of them as well as liposomes or their components, can also be used.

For oral use, tablets, coated tablets or capsules with talc and/or hydrocarbon vehicles or binding agents, such as, for example, lactose, corn or potato starch, are suitable. The use can also take place in liquid form, such as, for example, as juice, to which a sweetener optionally is added.

The dosage of the active ingredients can vary depending on the method of administration, age and weight of the patient, type and severity of the disease to be treated and similar factors. The daily dose is 0.001–0.034 mg, and the dose can be given as a single dose to be administered once or subdivided into 2 or more daily doses.

In the combination preparations according to the invention, the active ingredients can be present in a formulation or else in respectively separate formulations, and the entire dose is administered once or is divided into several doses.

The entire disclosures of all applications, patents and publications, cited above and below, and of corresponding application German P 41 23 106.6, filed Jul. 9, 1991, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

BRIEF DESCRIPTION OF THE DRAWINGS

The drawings represent in vivo data evidencing the effect of the invention.

Figure 1A:
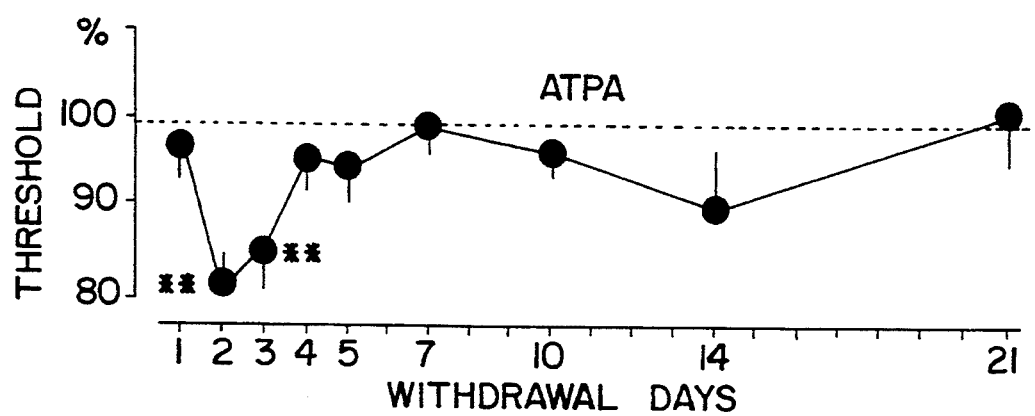
FIG. 1 represents the seizure threshold induced by ATPA, KA and NMDA in diazepam withdrawal.
Figure 1B:
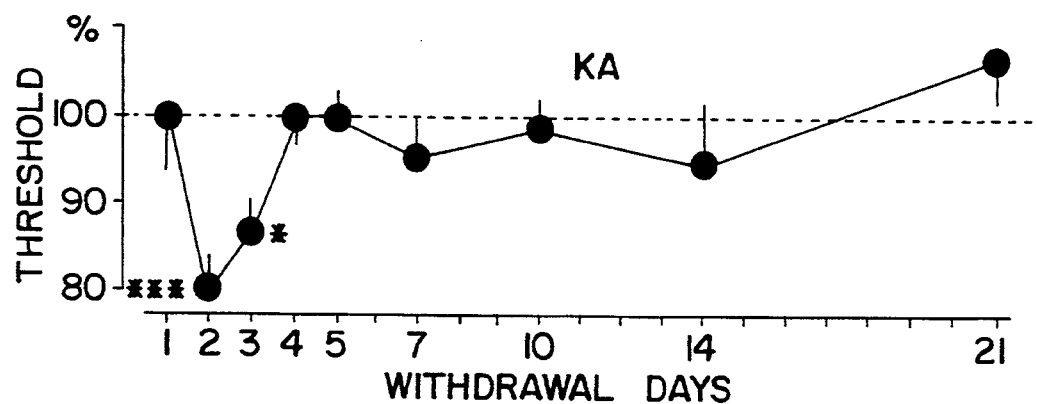
Figure 1C:
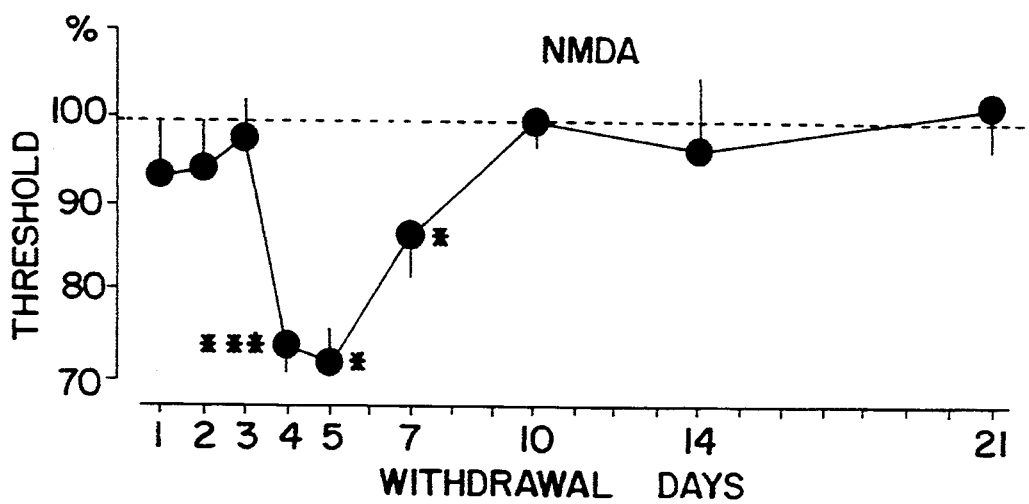
Figure 2A:
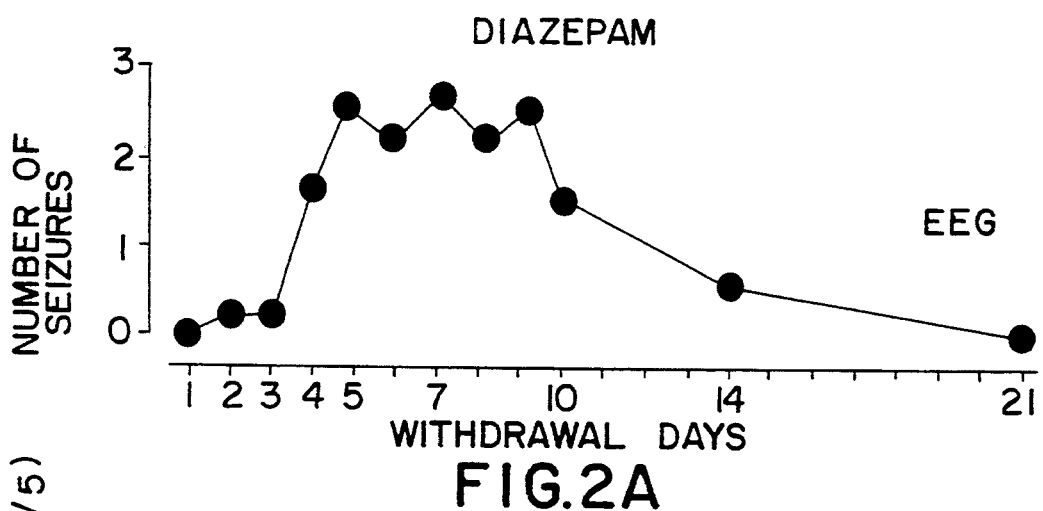
FIG. 2 represents, in diazepam withdrawal, number of seizures (EEG), muscle tone (EMG) and measure of anxiety, based on withdrawal days.
Figure 2B:
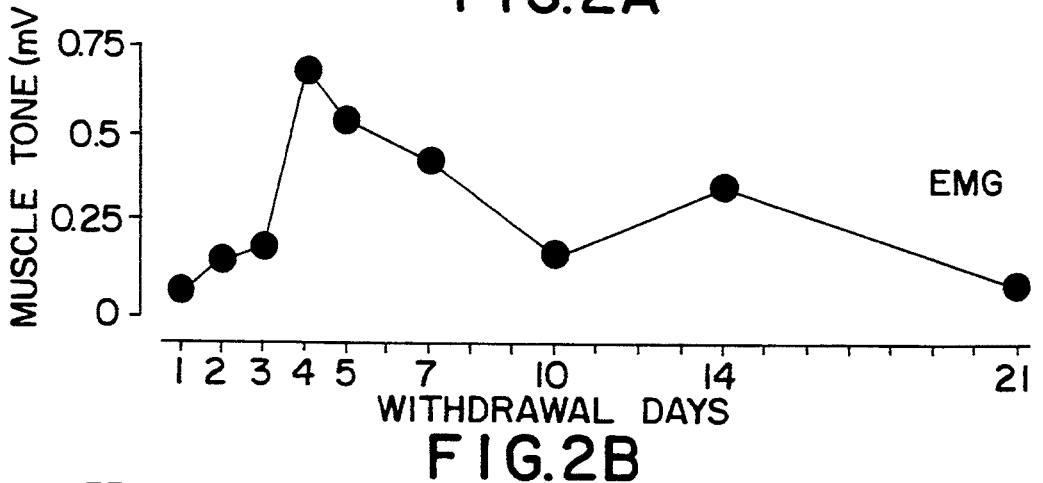
Figure 2C:
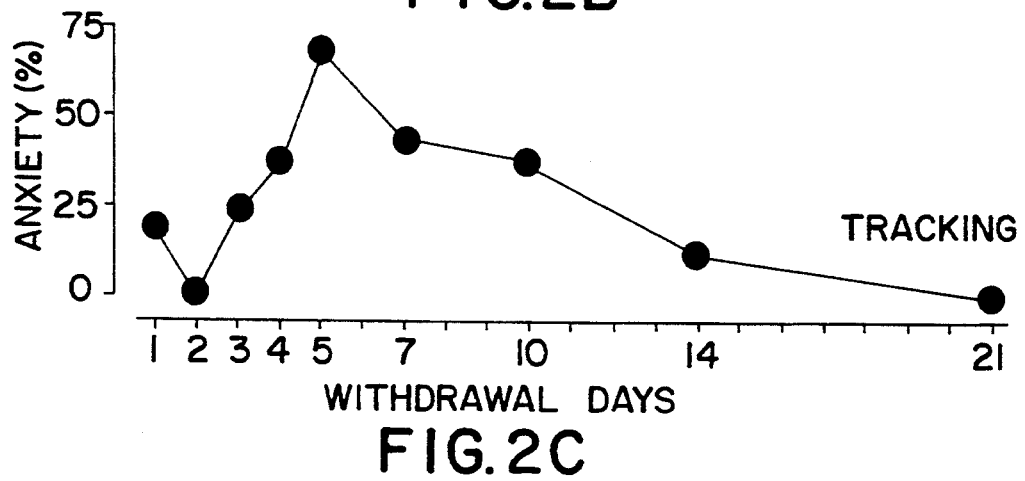
Figure 3A:
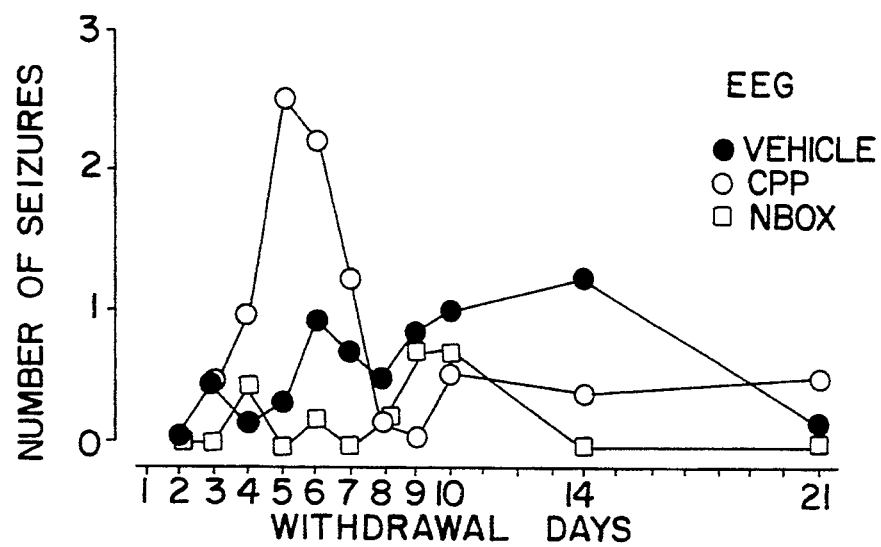
FIG. 3 represents seizure number, muscle tone and anxiety, with administration of control (vehicle), CPP and NBQX.
Figure 3B:
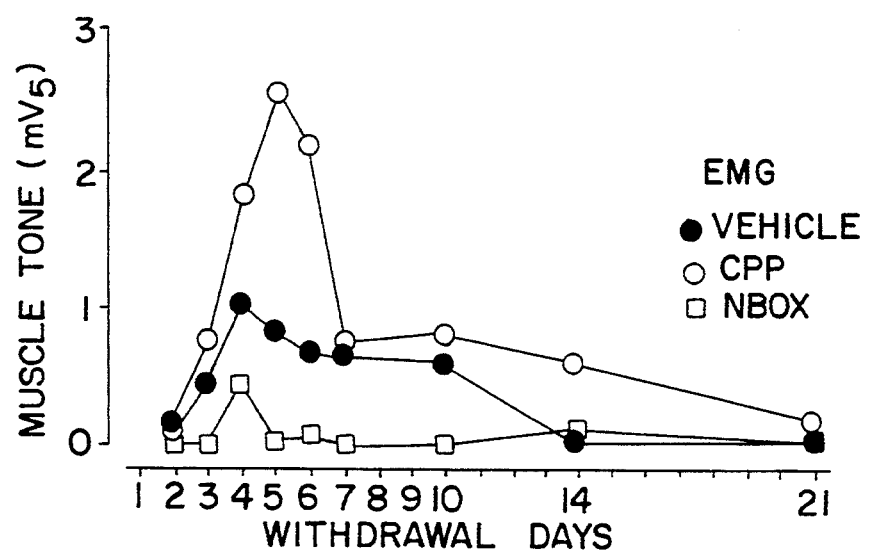
Figure 3C:
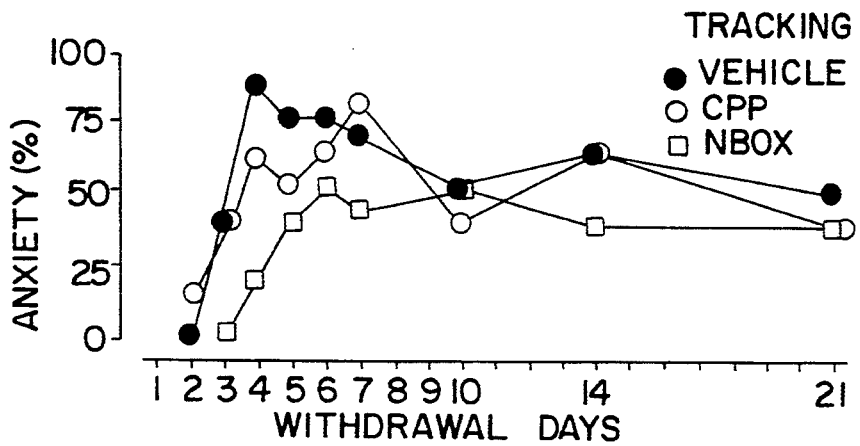

What is claimed is:

1. A method for the treatment of withdrawal caused by cessation of administration of a drug, said withdrawal having a first asymptomatic phase and a second symptomatic phase, comprising administering, during said first phase to a host in need thereof, an effective amount of a quisqualate or kainate receptor antagonist.

2. A method according to claim 1, comprising administering a quisqualate receptor antagonist.

3. A method according to claim 1, comprising administering a kainate receptor antagonist.

4. A method according to claim 2, wherein the drug is a narcotic.

5. A method according to claim 1, wherein the narcotic is a barbiturate or an opiate.

6. A method according to claim 1, wherein the narcotic is cocaine or heroin.

7. A method according to claim 1, wherein the drug is a benzodiazepine-receptor-binding agent.

8. A method according to claim 1, further comprising administering an NMDA receptor antagonist.

9. A method according to claim 8, wherein the administration of the NMDA receptor antagonist is subsequent to administration of the quisqualate or kainate receptor antagonist.

10. A method according to claim 9, wherein the NMDA receptor antagonist is administered in said second phase.

11. A method for prophylaxis of withdrawal caused by cessation of administration of a drug, said withdrawal having a first asymptomatic phase and a second symptomatic phase, comprising administering, prior to or during said first phase to a host in need thereof, an effective amount of a quisqualate or kainate receptor antagonist.

* * * * *